US009486192B2

(12) United States Patent
Pipenhagen

(10) Patent No.: US 9,486,192 B2
(45) Date of Patent: Nov. 8, 2016

(54) VASCULAR CLOSURE DEVICE WITH AUTOMATIC SUTURE CUTTER

(75) Inventor: Catherine A. Pipenhagen, Chanhassen, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 227 days.

(21) Appl. No.: 13/387,592

(22) PCT Filed: Jul. 27, 2010

(86) PCT No.: PCT/US2010/002102
§ 371 (c)(1),
(2), (4) Date: Mar. 9, 2012

(87) PCT Pub. No.: WO2011/014244
PCT Pub. Date: Feb. 3, 2011

(65) Prior Publication Data
US 2012/0158045 A1 Jun. 21, 2012

Related U.S. Application Data

(60) Provisional application No. 61/229,212, filed on Jul. 28, 2009.

(51) Int. Cl.
A61B 17/08 (2006.01)
A61B 17/00 (2006.01)
A61B 17/04 (2006.01)

(52) U.S. Cl.
CPC ....... A61B 17/0057 (2013.01); A61B 17/0467 (2013.01); A61B 2017/00654 (2013.01); A61B 2017/00659 (2013.01)

(58) Field of Classification Search
CPC .......... A61B 17/0057; A61B 17/0467; A61B 2017/00654; A61B 17/00659
USPC ............... 606/148, 213, 232, 144, 145, 139; 128/898
See application file for complete search history.

(56) References Cited

U.S. PATENT DOCUMENTS

| 5,179,963 A | 1/1993 | Berger |
| 6,007,563 A * | 12/1999 | Nash .................. A61B 17/0057 606/213 |
| 6,045,569 A | 4/2000 | Kensey et al. |

(Continued)

FOREIGN PATENT DOCUMENTS

| EP | 0534696 A1 | 3/1993 |
| WO | 2009039191 A2 | 3/2009 |
| WO | 2009052438 A2 | 4/2009 |

OTHER PUBLICATIONS

PCT International Search Report for PCT International Application No. PCT/US2010/002102, mailed Oct. 29, 2010.

Primary Examiner — Julie A Szpira
(74) Attorney, Agent, or Firm — Holland & Hart

(57) ABSTRACT

A tissue puncture closure device that includes an anchor (208, 508), a sealing pad (210, 510), a compaction member (212, 312, 412, 512), a suture (204, 504), and a suture cutting member (270, 472, 570). The compaction member is configured to compact the sealing pad toward the anchor. The suture is coupled to the sealing pad and anchor, and a portion of the suture extends through at least a portion of the compaction member. The suture cutting member is operable to cut the suture. The suture cutting member is operable within a portion of the compaction member to cut the suture.

22 Claims, 12 Drawing Sheets

(56) References Cited

U.S. PATENT DOCUMENTS

| | | |
|---|---|---|
| 6,090,130 A | 7/2000 | Nash et al. |
| 2003/0181926 A1 | 9/2003 | Dana et al. |
| 2006/0178682 A1 | 8/2006 | Boehlke |
| 2006/0229674 A1 | 10/2006 | Forsberg |
| 2006/0265006 A1* | 11/2006 | White et al. .................. 606/232 |
| 2007/0005081 A1* | 1/2007 | Findlay et al. ............... 606/148 |
| 2007/0150002 A1* | 6/2007 | Szabo et al. ................. 606/232 |
| 2009/0069844 A1 | 3/2009 | Green et al. |

* cited by examiner

VASCULAR CLOSURE DEVICE WITH AUTOMATIC SUTURE CUTTER

RELATED APPLICATION

This application claims the benefit of U.S. Provisional Patent Application No. 61/229,212, filed Jul. 28, 2009, which is hereby incorporated by reference herein in its entirety.

TECHNICAL FIELD

The present disclosure relates generally to medical devices and more particularly to vascular closure devices.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

Prior closure devices, such as the ones described in the above-mentioned patents, place a sealing pad at the tissue puncture site. Deployment of the sealing pad involves ejecting the pad from within a device sheath and compacting the pad down to an outer surface of the tissue puncture using a compaction member. After the sealing pad has been compacted against the tissue puncture, the suture is manually cut by the operator at a location outside of the patient. There is a need for improving the mechanism for cutting a suture of the closure device after compacting the sealing pad with a compaction member.

SUMMARY

The present disclosure is directed to closure devices, such as vascular closure devices, that include a cutting instrument that is an assembled part of the closure device. The cutting instrument may be a sterile cutting member. The cutting instrument may be operable between extended and retracted position to cut a suture at a location within the closure device. The suture may be cut by the cutting instrument at a location within a percutaneous incision. The cutting instrument may be positioned within a compaction tube of the closure device.

One aspect of the present disclosure relates to a tissue puncture closure device that includes an anchor, a sealing pad, a compaction member, a suture, and a suture cutting member. The compaction member is configured to compact the sealing pad toward the anchor. The suture is coupled to the sealing pad and anchor, and a portion of the suture extends through at least a portion of the compaction member. The suture cutting member is operable within the compaction member to cut the suture at a location adjacent a distal end portion of the compaction member.

The compaction member may include a suture path that exits the compaction member at an exit aperture along a sidewall of the compaction member. The suture path may include at least one change of direction between the distal end of the compaction member and the exit aperture. The suture cutting member may cut the suture at a location adjacent a distal end portion of the compaction member and within a percutaneous incision of a patient. The suture cutting member may have a generally tubular shape. The cutting member may be operable to cut the suture within the compaction member.

Another aspect of the present disclosure relates to a tissue puncture closure device adapted for partial insertion into and sealing of a tissue puncture in an internal tissue wall accessible through a percutaneous incision. The device includes an anchor, a sealing pad, a suture, a compaction member, and a suture cutting member. The anchor is disposed on a distal side of the internal tissue wall. The sealing pad is disposed on a proximal side of the internal tissue wall. The suture is coupled to the anchor, and the sealing pad is slidably disposed on the suture proximal of the anchor. The compaction member is positioned proximal of the sealing pad and is configured to compact the sealing pad toward the anchor to seal the tissue puncture. The suture cutting member is arranged parallel with the compaction member and adapted to cut the suture at a location within the percutaneous incision.

The tissue puncture closure device may further include an actuator coupled to the suture cutting member. In some embodiments, at least a portion of the suture cutting member is operable within the compaction member. The compaction member may define a suture path and a cutting member path that intersect each other. The suture may be positioned in the suture path and the suture cutting member is movable along the cutting member path to cut the suture. The suture path may begin at a distal end of the compaction member and terminates along a sidewall of the compaction member.

Another aspect of the present disclosure relates to a method of sealing a tissue puncture in an internal tissue wall accessible through a percutaneous incision using a tissue puncture closure device. The tissue puncture closure device includes an anchor, a sealing pad, a suture coupled to the anchor and the sealing pad, and a compaction member. The method includes inserting the tissue puncture closure device into the percutaneous incision, deploying the anchor through the tissue puncture, advancing the sealing member along the suture toward the anchor with the compaction member, and cutting the suture within the compaction member and within the percutaneous incision.

The tissue puncture closure device may include a suture cutting member, and cutting the suture may include moving the suture cutting member within the compaction member. The compaction member may define a suture path and a cutting member path that intersect each other, and the method may further include positioning the suture in the suture path and advancing a suture cutting member along the cutting member path. The step of cutting the suture may include advancing a tubular cutting member within the compaction member. The tissue puncture closure device may further include a tension structure configured to hold the suture in tension during the step of cutting the suture.

A further aspect of the present disclosure relates to a compaction assembly adapted for compacting a sealing member of a tissue puncture closure device. The compaction assembly includes a compaction member, a suture path, and a cutting member. The compaction member has a distal end portion configured to contact the sealing member. The suture path is defined in the compaction member and is adapted for passage of a suture member. The cutting member path is defined in the compaction member and intersects the suture path. The cutting member is movable along the cutting member path and is operable to cut a suture positioned in the suture path.

In some embodiments, the suture path includes at least one change of direction. The suture path and the cutting member path may intersect at a perpendicular angle. The cutting member may be generally tubular. The suture path may exit the compaction member along a sidewall of the compaction member.

Additional advantages and novel features will be set forth in the description which follows or can be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not limit the scope of the present disclosure.

Throughout the drawings, identical reference numbers designate similar, but not necessarily identical, elements.

DETAILED DESCRIPTION

Figure 1:
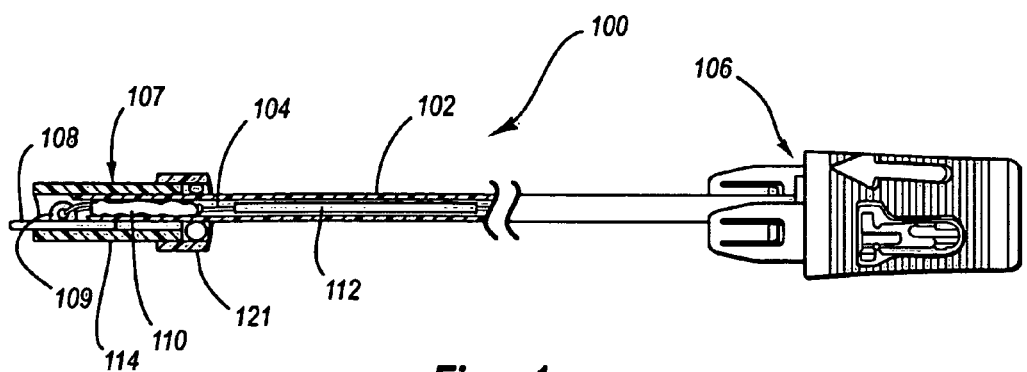
FIG. 1 is a perspective view of an example vascular closure device according to the present disclosure.

As mentioned above, vascular procedures are conducted throughout the world and require access to a vessel through a puncture. Often, the vessel is a femoral artery. To close the puncture following completion of the procedure, many times a closure device is used to sandwich the puncture between an anchor and a sealing pad. A suture is often used to couple together the anchor and sealing pad. A force may be applied along the suture to draw the anchor and sealing pad toward each other as the sealing pad is compacted against the puncture. Typically, the suture is manually cut at a location outside of the patient after confirmation that the puncture has been sealed. Cutting the suture releases the anchor and sealing pad from the remaining portions of the closure device. Leaving a length of suture protruding through the patient's skin surface may result in complications such as, for example, infections that may arise where the suture exits the patient's skin. Further, requiring the extra step of manually cutting the suture with an instrument separate from the closure device requires additional time and complexity to the procedure.

The present disclosure describes methods and apparatus that facilitate cutting of the suture using features that are integral with the closure device. The present disclosure further describes methods and apparatus that facilitate cutting of the suture within a percutaneous incision at a location below the patient's outer skin surface. Some aspects of the present disclosure relate to built-in sterile cutting instruments. The cutting member that provides cutting of the suture may be a sterile instrument that is an assembled part of the closure device. The cutting member may have a cutting surface along a distal end thereof that cuts the suture when advanced distally.

While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engageable" are also used broadly to mean interlock, mesh, or contact between two structures or devices. Likewise "disengage" or "disengageable" means to remove or capable of being removed from interlock, mesh, or contact. A "tube" is an elongated device with a passageway. The passageway can be enclosed or open (e.g., a trough). A "lumen" refers to any open space or cavity in a bodily organ, especially in a blood vessel. The words "including" and "having," as used in the specification, including the claims, have the same meaning as the word "comprising."

Referring to FIGS. 1-5, a vascular puncture closure device 100 is shown according to the prior art. Some example closure devices are disclosed in U.S. Published Patent Application Nos. 2006/0265006 and 2006/0229674, which applications are incorporated in their entireties by this reference. The vascular puncture closure device 100 includes a carrier tube 102 with a filament or suture 104 extending at least partially therethrough. The closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
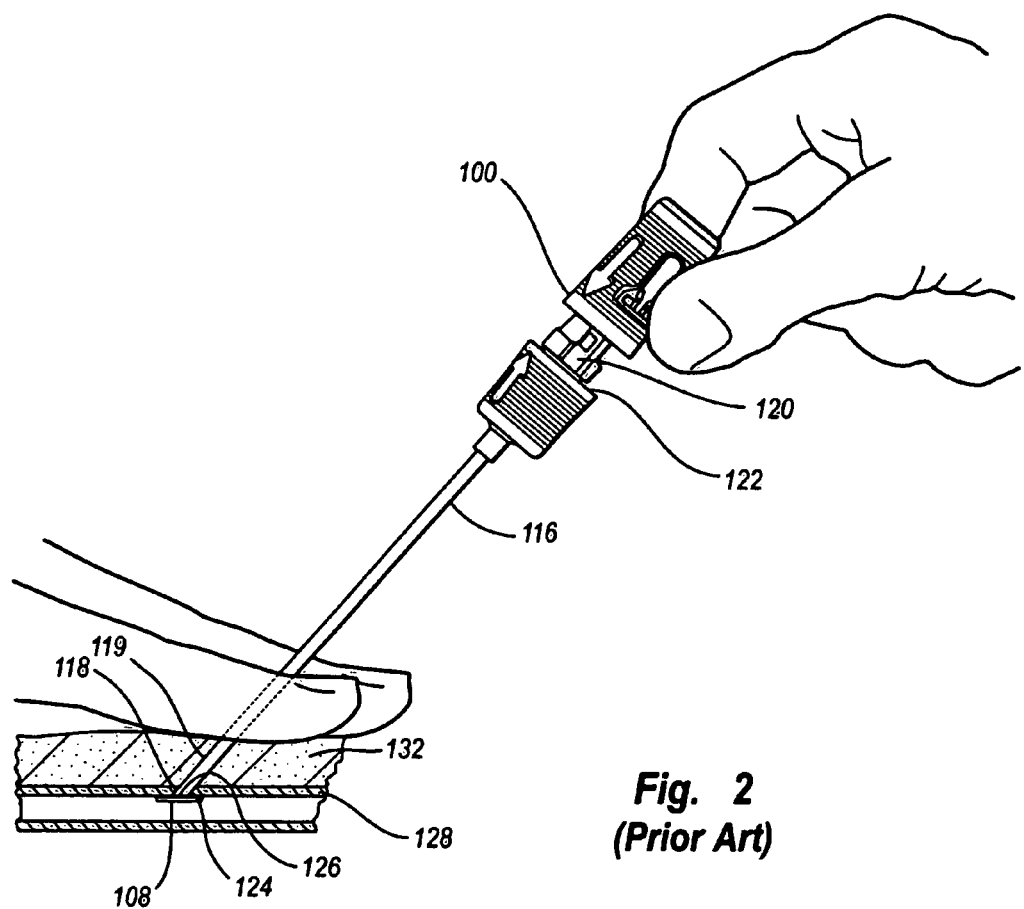
FIG. 2 is a perspective view of the vascular closure device shown in FIG. 1 with an anchor disposed in a vessel.
Figure 3:
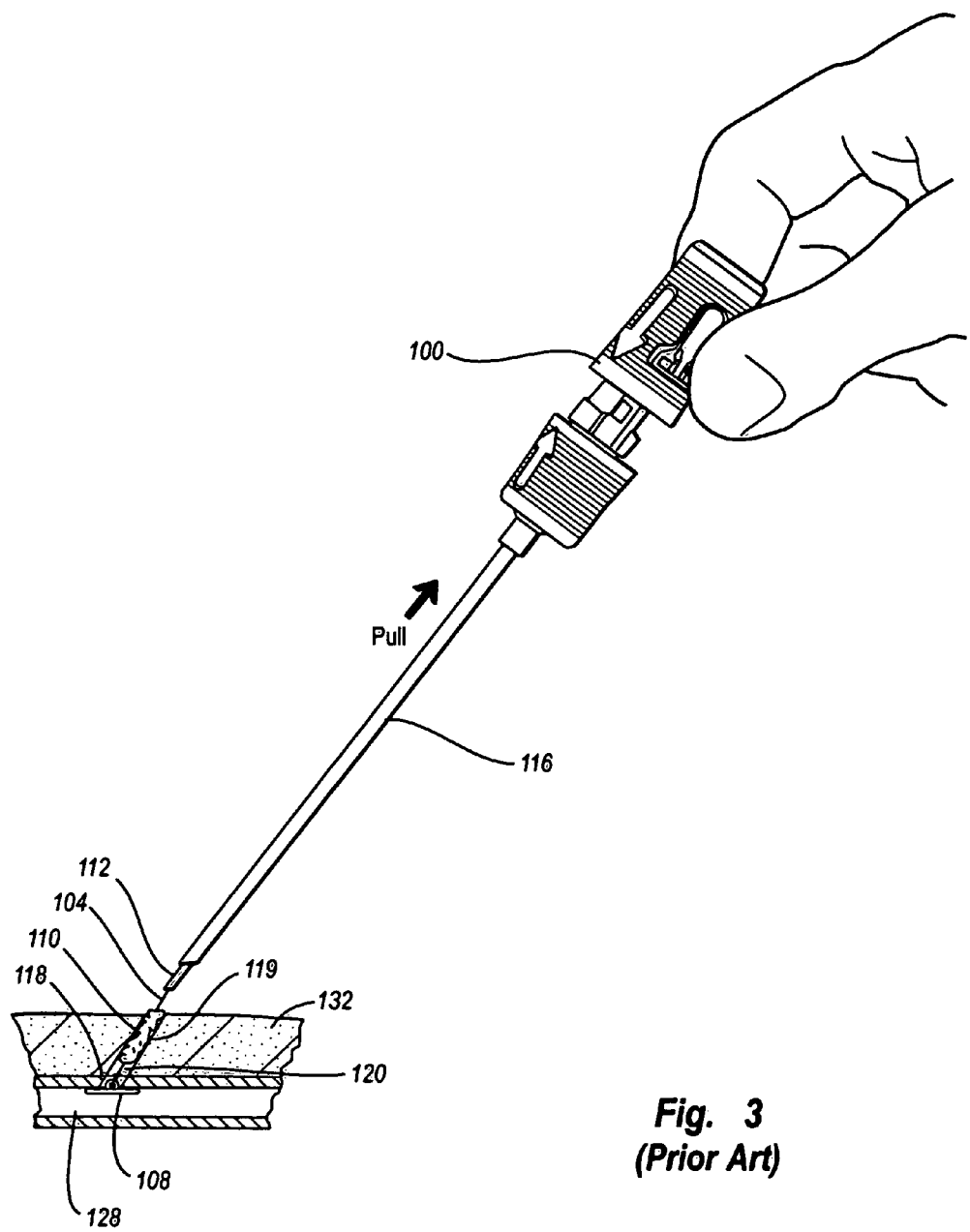
FIG. 3 is a perspective view of the vascular closure device shown in FIG. 1. with the sealing pad disposed in the percutaneous incision.
Figure 4:
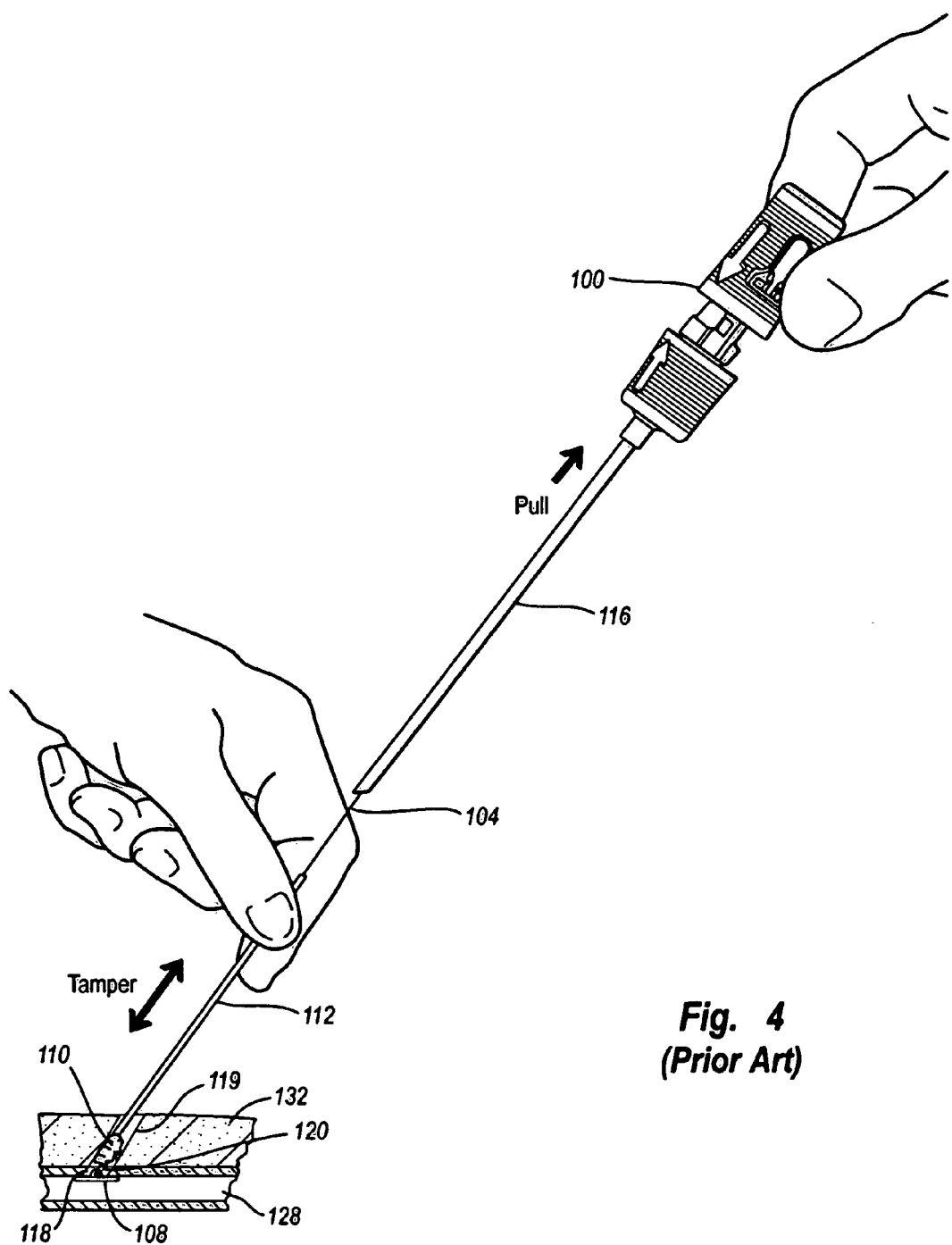
FIG. 4 is a perspective view of the vascular closure device shown in FIG. 1 with the operator compacting the sealing pad with a compaction member.

The flush arrangement of the anchor 108 and carrier tube 102 allows the anchor 108 to be inserted into a procedure sheath such as insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (see FIG. 1) includes an oversized head 121 that prevents the bypass tube 114 from passing through an internal passage of the insertion sheath 116. Therefore, as the puncture closure device 100 is inserted into the insertion sheath 116, the oversized head 121 bears against a surface 122 of insertion sheath 116.

Further insertion of the puncture closure device 100 results in sliding movement between the carrier tube 102 (see FIG. 1) and the bypass tube 114, and releases the anchor 108 from the bypass tube 114 (see FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, ejecting the collagen pad 110 from the carrier tube 102 into the incision tract 119 and exposing the compaction member 112. With the compaction member 112 fully exposed as shown in FIG. 4, the collagen pad 110 is manually compacted, and the anchor 108 and collagen pad 110 are cinched together and held in place with the self-tightening slip-knot on the suture 104. Thus, the tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

It may be difficult to eject and compact the collagen pad 110 using the typical tissue puncture closure device 100 described above. The insertion sheath 116 resists deformation as the collagen pad 110 is ejected from the carrier tube and compaction cannot commence until the sheath 116 has been removed so as to expose the compaction member 112 for manual grasping. Under certain conditions, removal of the sheath 116 prior to compacting the collagen pad 110 causes the collagen pad 110 to retract or displace proximally from the tissue puncture 118, creating an undesirable gap 120 between the collagen pad 110 and the puncture 118. The gap 120 may remain even after compacting as shown in FIG. 4, and sometimes results in only a partial seal and bleeding from the tissue puncture 118.

Figure 5:
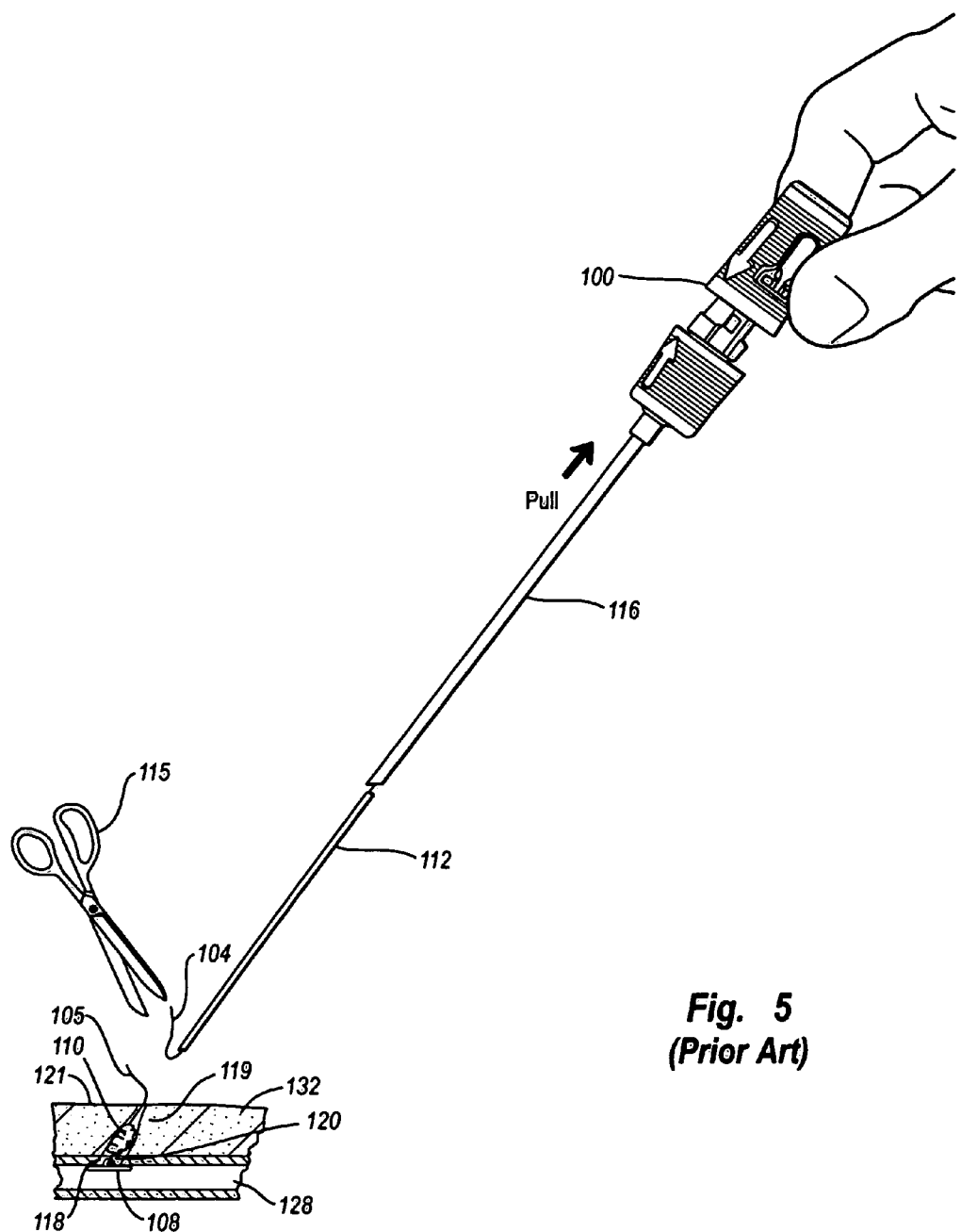
FIG. 5 is a perspective view of the vascular closure device shown in FIG. 1 with the suture being manually cut at a location outside of the percutaneous incision.

FIG. 5 illustrates cutting of the suture 104 after compaction of the collagen pad 110 is completed. Typically, the suture 104 is cut using a cutting instrument 115 that is separate and distinct from the vascular puncture closure device 100. The cutting instrument 115 may be, for example, scissors or a sterile scalpel. A free or cut end 105 of the suture 104 is located outside of the percutaneous incision 119. Thus, the suture 104 passes through an outer skin surface 121.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Figure 6:
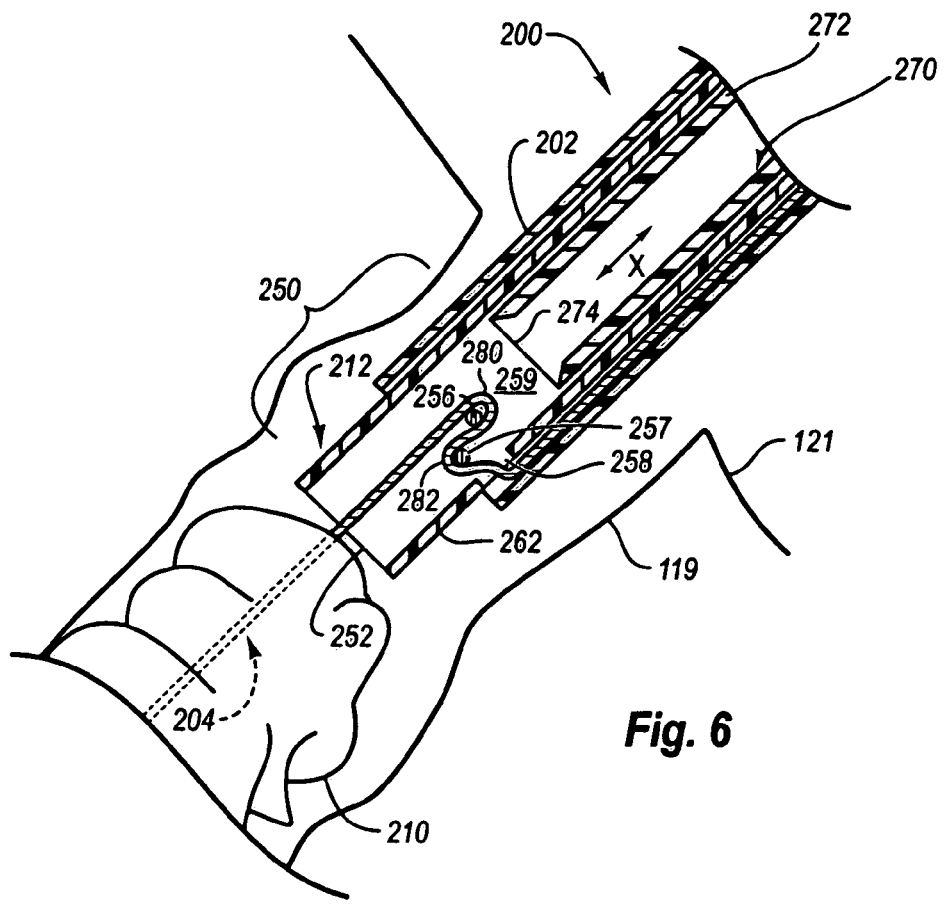
FIG. 6 is a cross-sectional view of a distal end portion of another vascular closure device that includes a suture cutter disposed within the compaction member.
Figure 7:
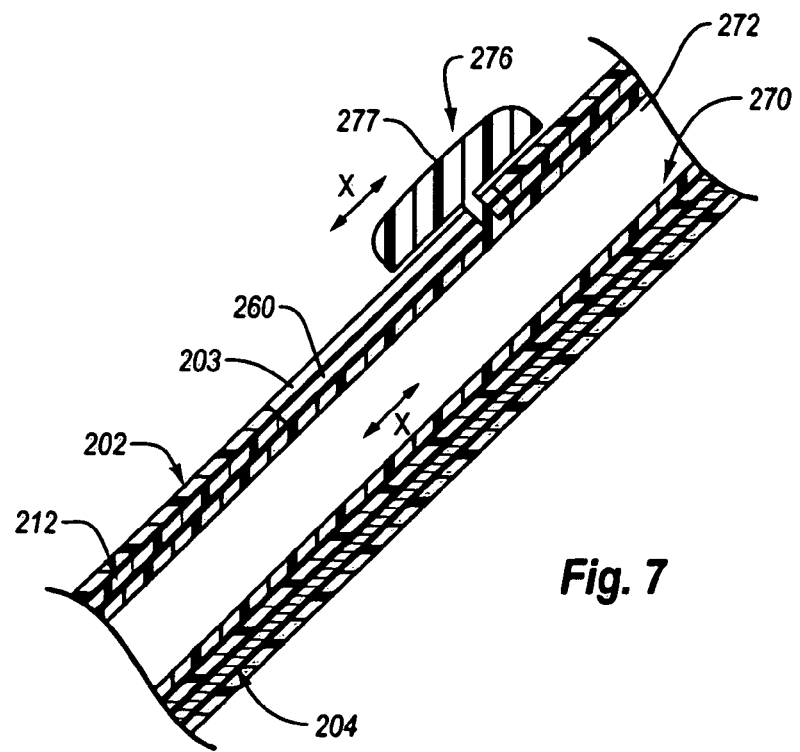
FIG. 7 is a cross-sectional view of a proximal end portion of the vascular closure device shown in FIG. 6.
Figure 11:
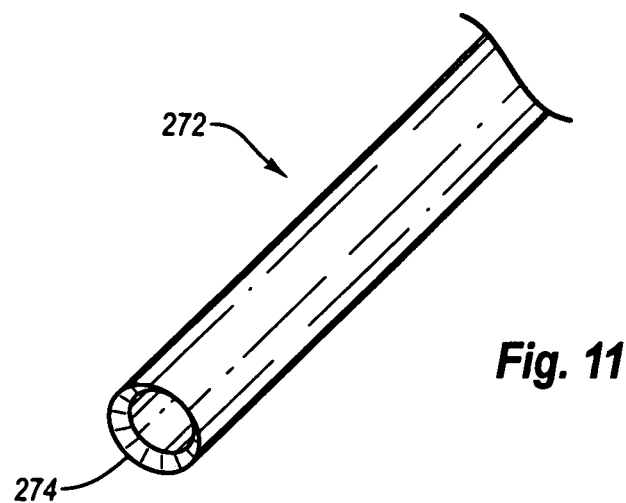
FIG. 11 is a perspective view of the suture cutter shown in FIG. 6.

Referring now to FIGS. 6, 7, and 11, an alternative compaction member 212 and suture cutter assembly 270 are shown and described. The compaction member 212 includes a distal end portion 250, a distal end opening 252, first and second suture track members 256, 257, a suture side exit 258 defined in a sidewall 262, and a cutter track 259. The distal end portion 250 is shown in contact with a compacted sealing pad 210 after the compaction member 212 has been used to compact the sealing pad 210 as described above with reference to FIGS. 1-5. A suture 204 extends into the distal end opening 252 and passes over the first and second suture track members 256, 257 before exiting out of the suture side exit 258. The suture 204 extends in a proximal direction in a space defined between an outer surface of the sidewall 262 and an inner surface of the carrier tube 202.

The pathway of the suture 204 around the first and second suture track members 256, 257 defines first and second bends 280, 282 in the suture 204. The bends 280, 282 may define a change of direction for the suture and may define in part a suture path with at least one change of direction. In some arrangements, the bends 280, 282 define at least two changes of direction. Inclusion of the first and second bends 280, 282 may provide additional friction along the length of the suture 204 so that the suture 204 may maintain some tension while other operations of the vascular closure device are carried out. Maintaining some tension in the suture 204 may also be helpful in the cutting step performed by engaging the suture 204 with a suture cutter as described in further detail below.

The cutter track 259 is defined, at least in part, internal of the sidewall 262 of the compaction member 212. In the embodiment of FIGS. 2-7, the cutter track 259 is defined in part by the hollow, internal lumen of the compaction member 212. Typically, the cutter track 259 is defined between the first and second track members 256, 257 and the sidewall 262 of the compaction member 212. The portion of the sidewall 262 adjacent to the suture side exit 258 may provide a fixed surface against which the suture 204 is supported while the suture 204 is cut by the suture cutting assembly 270 moving along the cutter track 259.

The suture cutter assembly 270 includes a cutting tube 272 as shown in at least FIG. 11. The suture cutting assembly 270 also includes a cutting surface 274 arranged along a distal end thereof. The generally cylindrical shape of the cutting tube 272 promotes sliding movement within the hollow lumen defined by the compaction member 212.

The suture cutter assembly 270 may include an actuator 276 that is positioned proximal of the distal end portion 250 of the compaction member 212. The actuator 276 may include an actuator surface 277 that the operator engages while applying a force in the cutter direction X, as shown in FIG. 7. The compaction member 212 may include an actuator slot 260 and the carrier tube 202 may include an actuator slot 203. The actuator 276 extends through, or is at least accessible through, the actuator slots 260, 203 for operation by the operator.

In at least one example, the actuator 276 is constructed as a sliding thumb actuated member that moves the cutting tube 272 internal of the compaction member 212. Many other actuator constructions are possible. In at least one example, the actuator 276 is associated with a handle portion of the vascular closure device. In at least some examples, actuation of the actuator 276 occurs automatically upon completion of, for example, compacting the sealing pad 210 with the compaction member 212 using an automatic compaction assembly. An example thumb actuated suture cutting member construction is disclosed in U.S. Published Patent Application No. 2006/0178682, which is herein incorporated in its entirety by this reference.

Figure 8:
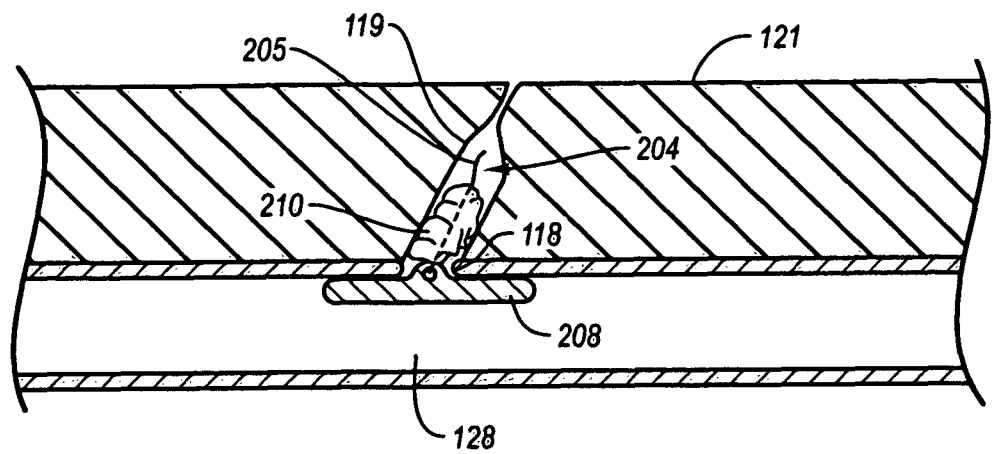
FIG. 8 is a cross-sectional view of the anchor, sealing member and suture of the vascular closure device shown in FIG. 6 with the suture cut within the percutaneous incision.

Referring now to FIG. 8, an anchor 208 and sealing pad 210 are shown lodged within a percutaneous incision 119 to seal an arterial puncture 118 in a vessel 128. A free end 205 of a suture 204 is shown positioned within the percutaneous incision 119 below a skin surface 121. The suture 204 was cut using the suture cutter assembly 270, described with reference to FIGS. 6 and 7, while the distal end portion 250 of the compaction member 212 remained at least partially positioned within the percutaneous incision 119. As described herein, it is possible for the suture 204 to be cut using features of the vascular closure device 100 without the need for instruments that are separate from the closure device 100 (e.g., such as the cutting instrument 115 shown in FIG. 5).

Figure 9:
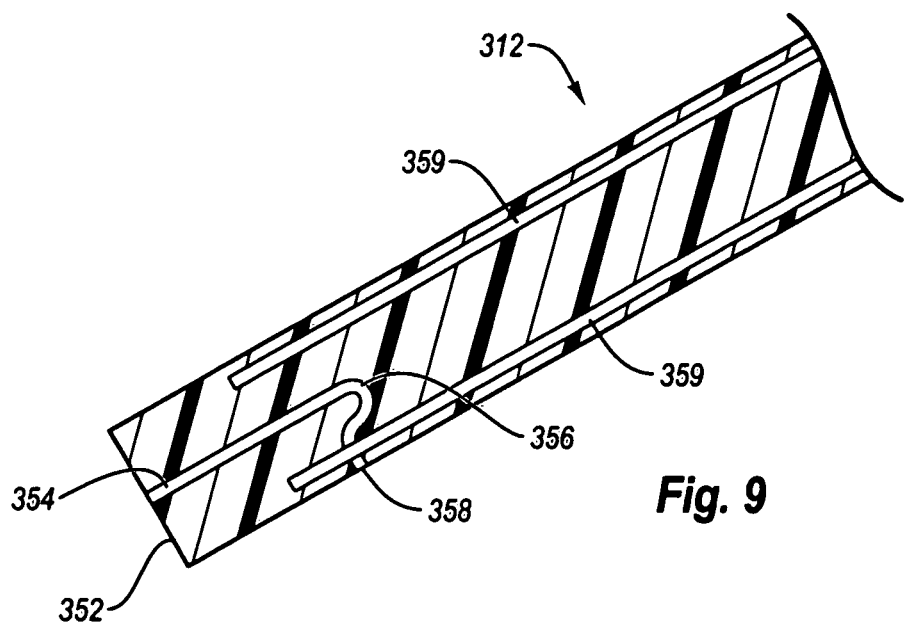
FIG. 9 is a cross-sectional view of a distal end portion of another example compaction member according to the present disclosure.

Referring now to FIG. 9, another example compaction member 312 is shown and described. The compaction member 312 includes a distal end 352, a suture track 354, a suture track bend 356, a suture side exit 358, and a cutter track 359. The compaction member 312 is shown as a generally solid member having the plurality of tracks 354, 359 defined therein. A suture (not shown) may be advanced through the suture track 354 from the distal end 352 to the suture side exit 358. The proximal portion of the suture may be advanced proximally and used in, for example, operation of an automatic compacting device. The proximal portion of the suture may extend proximally between, for example, an outer surface of the compaction member 312 and an inner surface of a carrier tube 202.

The cutter track 359 may be sized for passage of a cutting tube of a suture cutter assembly to pass therethrough. The cutter track 359 intersects the suture track 354. As a cutting tube or other cutting member (not shown) passes distally through the cutter track 359 toward the distal end 352, the cutting member may cut a suture that resides in the suture track 354 and is exiting the suture side exit 358.

Figure 10:
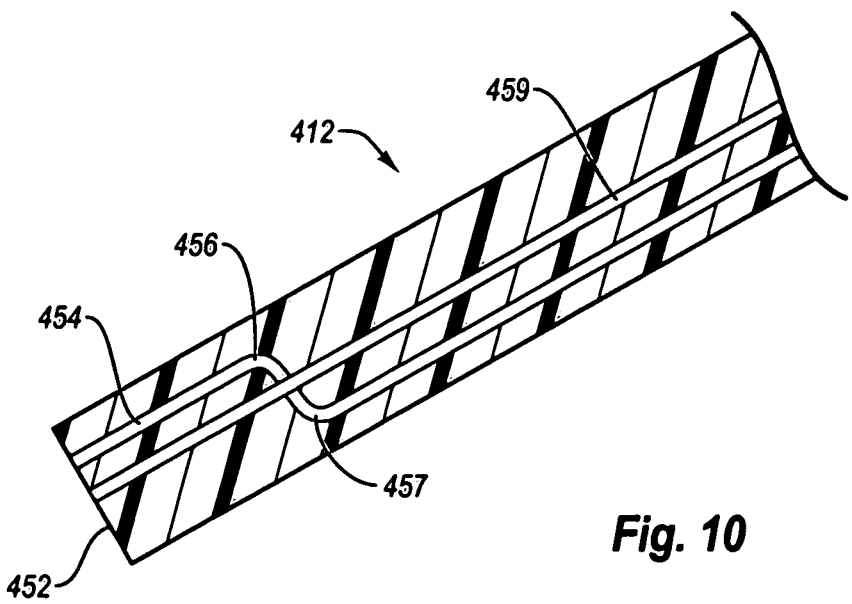
FIG. 10 is a cross-sectional view of a distal end portion of another example compaction member according to the present disclosure.

Referring now to FIG. 10, a further example compaction member 412 is shown and described. The compaction member 412 includes a distal end 452, a suture track 454 having first and second suture track bends 456, 457, and a cutter track 459. The suture track 454 remains within the compaction member 412 at least along a distal end portion of the compaction member 412. The suture track 454 intersects with the cutter track 459 at a location between the track bends 456, 457. A cutting tube or other cutting member of a suture cutting assembly (not shown) moving distally through the cutter track 459 may cut a suture that is positioned in the suture track 454 between the first and second track bend portions 456, 457.

In at least the embodiments of FIGS. 9 and 10, the suture tracks 354, 454 and cutter tracks 359, 459 may be formed in the compaction member using a cutting process, such as laser cutting. In other examples, the tracks 354, 454, 359, 459 may be formed using a molding process, casting, etching, or other forming technique. Some example cutting techniques and suture track designs are disclosed in U.S. Published Patent Application No. 2006/0178682.

Figure 12:
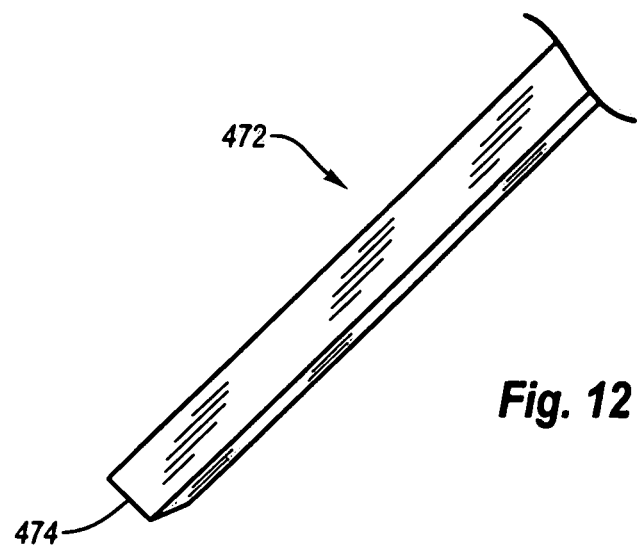
FIG. 12 is a perspective view of another example suture cutter according to the present disclosure.
Figure 13:
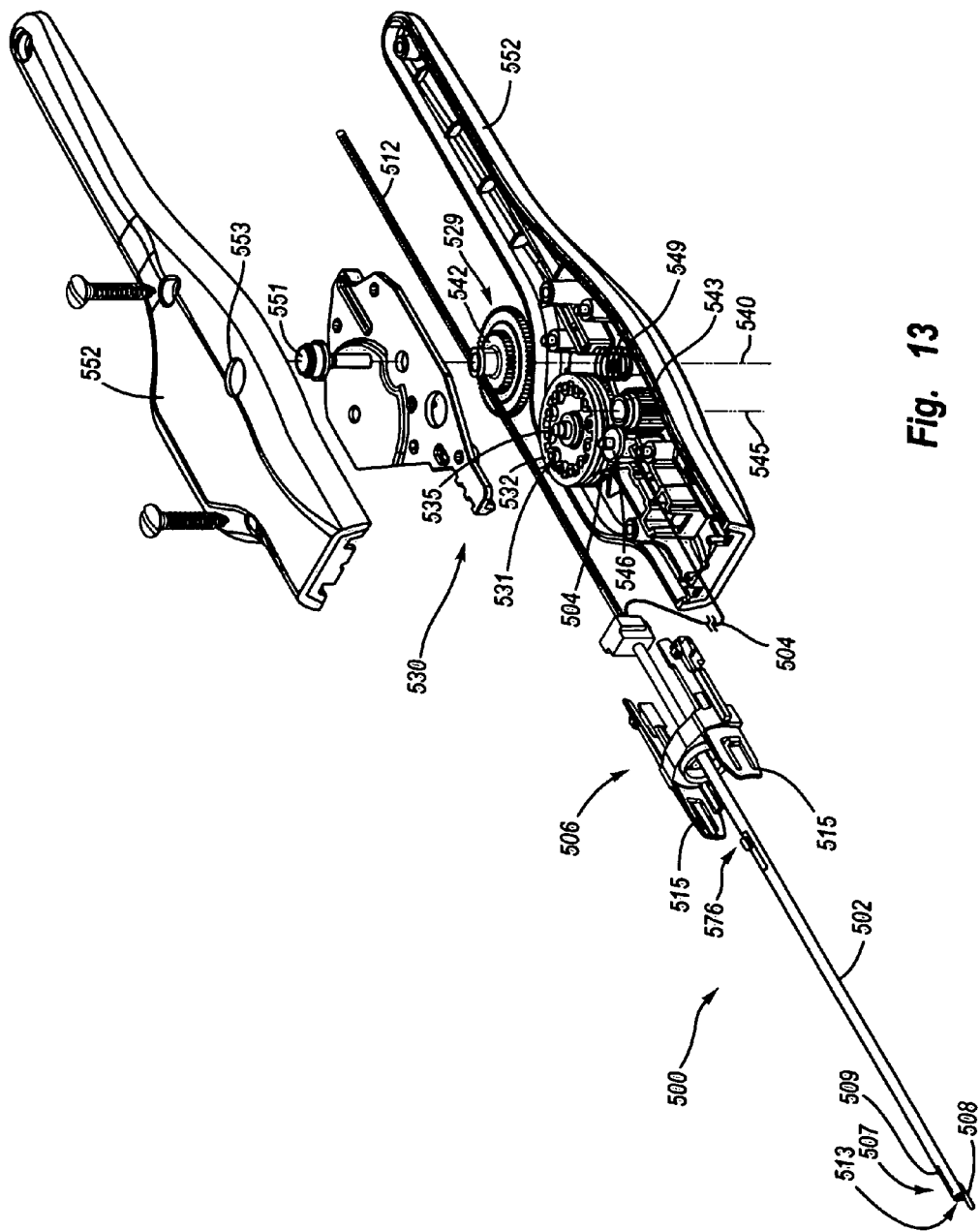
FIG. 13 is an exploded perspective view of another example vascular closure device that includes the suture cutter of FIGS. 6-7.

The cutting tube or cutting member of the suture cutter assembly may have various shapes and sizes. FIG. 11 illustrates a cutting tube 272 having a generally cylindrical shape with a circular cross-section. The cutting tube 272 defines a cutting surface 274 that is generally circular. Other arrangements and constructions are possible for the cutting member (i.e., cutting tube 272). FIG. 12 illustrates an elongate cutting member 472 having a generally rectangular cross-section and a linear cutting surface 474 along a distal end thereof. The elongate cutting member 472 may be particularly useful with the cutting track 459 of the compaction member 412.

The example compaction members and suture cutter assemblies disclosed above with reference to FIGS. 6-12 may be incorporated into a vascular closure device 500 that includes an automatic compaction assembly (see FIGS. 13-16). FIGS. 13-16 illustrate the closure device 500 assembled and inserted through a procedure sheath 516 and into a vessel 128. The closure device 500 includes a first or proximal end portion 506 and a second or distal end portion 507. A carrier tube 502 extends from the proximal end portion 506 to the distal end portion 507 and includes an outlet 513 at the distal end portion 507. The distal end portion 507 may include a slit 509.

The procedure sheath 516 is designed for insertion through a percutaneous incision 119 and into the vessel 128 through a vessel puncture 118. At the distal end portion 507 of the carrier tube 502 there is an anchor 508 and a sealing pad 510. The anchor 508 may be seated inside the vessel 128 adjacent to the puncture 118. The anchor 508 is preferably made of a biologically resorbable polymer. A sealing pad 510 is positioned proximal of the anchor 508 and is typically formed of a compressible sponge, foam, or fibrous mat made of a non-hemostatic biologically resorbable material such as collagen. The sealing pad 510 may be configured in any shape so as to facilitate sealing the tissue puncture 518.

The sealing pad 510 and anchor 508 are connected to one another by a filament or suture 504 that is also biologically resorbable. The anchor 508 is initially arranged adjacent to and exterior of the distal end portion 507 of the carrier tube 502 (see FIG. 13), while the sealing pad 510 is initially disposed within the carrier tube 502 (see FIG. 14). The suture 504 extends distally from the first end portion 506 of the closure device 500 through the carrier tube 502. The suture 504 may be threaded through one or more perforations in the sealing pad 510, through a hole in the anchor 508, and proximally back to the sealing pad 510. The suture 504 is preferably threaded again through a perforation or series of perforations in the sealing pad 510. The suture 504 may also be threaded around itself to form a self-tightening slip-knot. The suture 504 may thus connect the anchor 508 and the sealing pad 510 in a pulley-like arrangement to cinch the anchor 508 and the sealing pad 510 together when the carrier tube 502 is pulled away from the anchor 508 and the sealing pad 510. The anchor 508 and the sealing pad 510 sandwich and lock the anchor and pad together, sealing the tissue puncture 118.

The carrier tube 502 houses a compaction member 512 for advancing the sealing pad 510 along the suture 504 and toward the anchor 508. The compaction member 512 is shown located partially within the carrier tube 502 and proximal of the sealing pad 508. The compaction member 512 also extends through a handle 552 of the closure device 500. The compaction member 512 is preferably an elongated tubular or semi-tubular rack that may be rigid or flexible and formed of any suitable material. For example, according to one embodiment, the compaction member 512 is made of polyurethane. The suture 504 extends through at least a portion of the compaction member 512. The suture 504 is not directly connected to the compaction member 512. Accordingly, the suture 504 and the compaction member 512 may slide past one another.

The suture 504 attaches to an automatic tamping assembly. The automatic tamping assembly may include an automatic driving mechanism 530 or other transducer, and the compaction member 512. The automatic driving mechanism 530 is located within the housing or handle 552 at the first end portion 506 of the closure device 500. The compaction member 512 may comprise a rack receptive of gear teeth of the automatic driving mechanism.

The closure device 500 may further include a cutting member 570 (see FIG. 16) arranged and configured to cut the suture 504. The cutting member 570 may be constructed and operable similar to the cutting member 570 described above with reference to FIGS. 6-12. For example, the cutting member 570 may be positioned within the compaction member 512. The cutting member 570 may include a cutting surface at a distal end thereof. The cutting member 570 may be coaxial with the compaction member 512 and may be arranged parallel with the compaction member 512.

Figure 14:
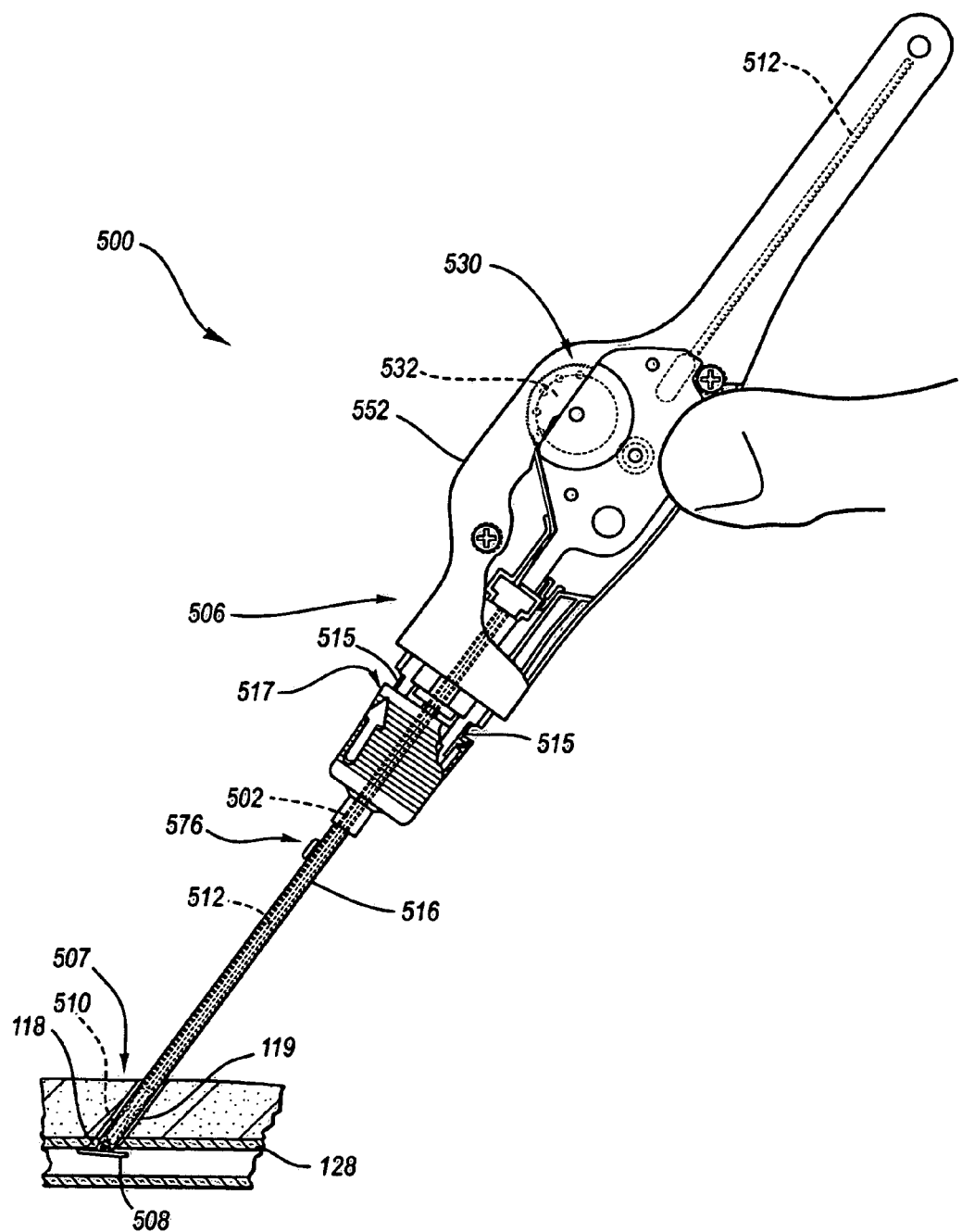
FIG. 14 is a perspective view of the vascular closure device shown in FIG. 13 with an anchor disposed in a vessel.
Figure 15:
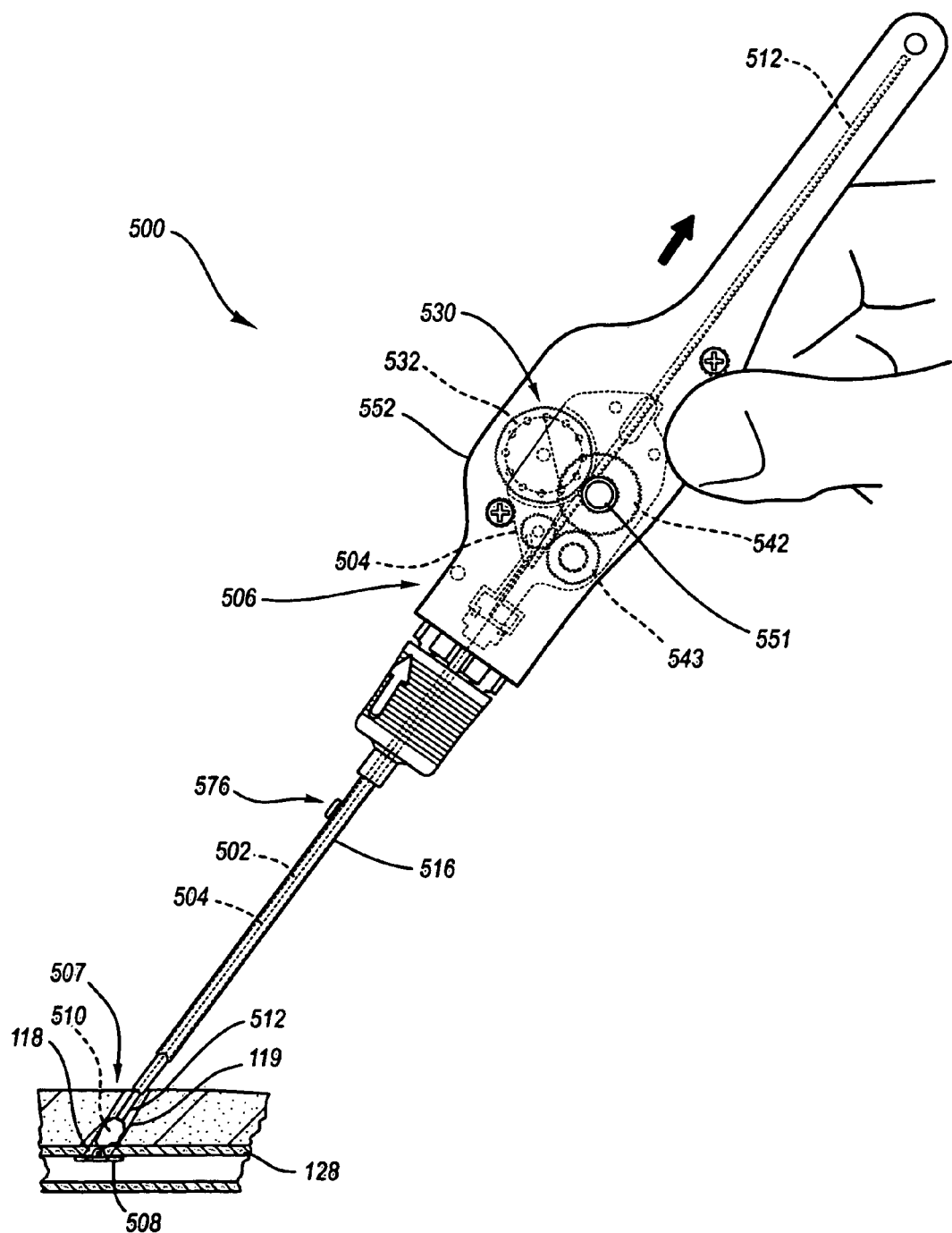
FIG. 15 is a perspective of the vascular closure device shown in FIG. 13 with the sealing pad compacted in the percutaneous incision.
Figure 16:
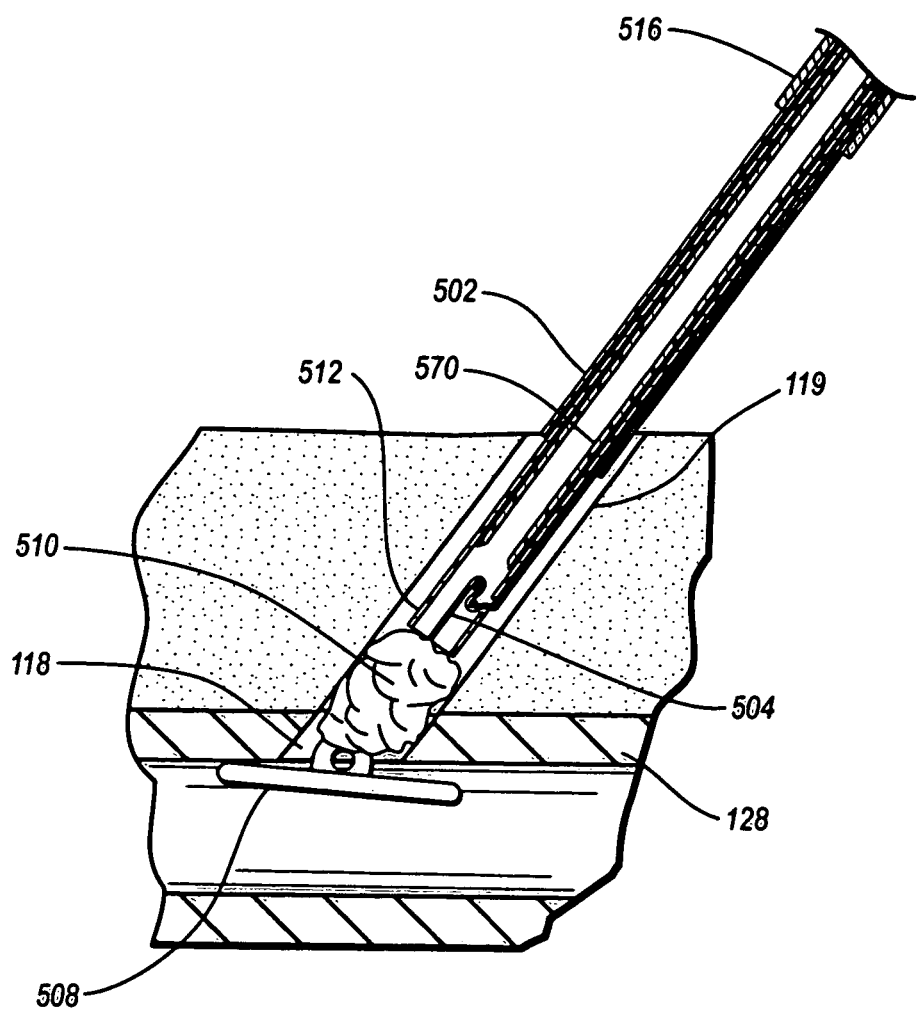
FIG. 16 is a detailed view of the vascular closure device shown in FIG. 15.

In practice, the carrier tube 502 of the closure device 500 is inserted into the insertion sheath 516, which is already inserted within the vessel 128 (see FIGS. 14-16). As the closure device 500 and the associated closure elements are inserted into the procedure sheath 516, the anchor 508 passes through and out of the distal end of the procedure sheath 516 and is inserted into the vessel 128. After the anchor 508 passes out of the distal end of the procedure sheath 516 it tends to deploy or rotate to the position shown in FIG. 14. The closure device 500 may also be partially withdrawn from the insertion sheath 516, catching the anchor 508 on the distal end of the insertion sheath 516 and rotating it to the position shown in FIG. 14. The closure device 500 preferably includes a pair of biased fingers 515 that are lockingly received by a matching pair of recesses 517 in the procedure sheath 516. The locking arrangement between the biased fingers 515 and matching recesses 517 preferably fixes the position of the handle 552 relative to the procedure sheath 516.

Following deployment of the anchor 508, the handle 552 and the insertion sheath 516 are withdrawn together. Withdrawing the handle 552 causes the anchor 508 to anchor itself within the vessel 128. With the anchor 508 anchored within the vessel 128 at the puncture site 518, further retraction of the handle 552 and insertion sheath 516 tends to pull the sealing pad 510 out from the distal end portion 507 of the carrier tube 502, thereby depositing the pad 510 within the incision tract 119. Retraction of the handle 552 and insertion sheath 516 causes the insertion sheath 516 to retract with respect to the carrier tube 502.

The distal end portion 507 of the carrier tube 502 is exposed within the incision tract 519 as the handle 552 and the procedure sheath 516 are retracted. The carrier tube 502 retains its position relative to the puncture 118 until the handle 552 and the procedure sheath 516 have been retracted a predetermined distance. Relative movement between the handle 552/procedure sheath 516 and the carrier tube 502 is facilitated by a sliding mount arrangement between the automatic driving mechanism 530 and the handle 552. In alternative arrangements, the automatic driving mechanism 530 is fixed to the handle 552.

The automatic driving mechanism 530 (which is attached to the carrier tube 502) is typically free floating or displaceable and slides relative to the handle 552 as the handle 552 and the procedure sheath 516 are retracted. The automatic driving mechanism 530 may initially be held in a first position relative to the handle 552 as shown in FIG. 14. The automatic driving mechanism 530 may release automatically when a sufficient predetermined force is applied between the handle 552 and the automatic driving mechanism 530. For example, with the anchor 508 deployed, a retraction force provided by a user to the handle 552 causes the automatic driving mechanism 530 to slide distally. Accordingly, retraction of the handle 552 retracts the procedure sheath 516 (which is fixedly connected to the handle 552), but the automatic driving mechanism 530 and the carrier tube 502 slide relative to the handle 552 and therefore remain in position with respect to the puncture 518.

When the automatic driving mechanism 530 reaches a distal rest position relative to the handle 552 (see FIG. 15), further retraction of the handle 552 withdraws the carrier tube 502 as well, ejecting and compacting the sealing pad 510 automatically as shown in FIGS. 15-16. Unlike previous closure devices that require a separate, manual tamping procedure following the deposition of the sealing pad 510, the closure device 500 automatically compacts the sealing pad 510. The sealing pad 510 is compacted while the carrier tube 502 is being withdrawn, reducing or eliminating any gaps that may otherwise occur between the sealing pad 510 and the puncture 518 in the vessel 128.

In addition, by placing tension on or pulling the suture 504 away from the puncture tract 519, the suture 504 may cinch and lock (with a slip knot or the like) together the anchor 508 and the sealing pad 510, sandwiching the vessel wall between the anchor 508 and sealing pad 510. The force exerted by the compaction member 512 and the cinching together of the anchor 508 and sealing pad 510 by the filament 504 also causes the sealing pad 510 to deform radially outward within the puncture tract 519 and function as an anchor on the proximal side of the tissue puncture site 518 as shown in FIGS. 15-16.

The compaction member 512 is automatically driven toward the sealing pad 510 by the automatic driving mechanism 530. One embodiment of the automatic driving mechanism 530 is shown in detail in FIGS. 13-16. The automatic driving mechanism 530 may comprise a gearbox assembly 529, and the gearbox assembly 529 may be selectably disengageable.

The suture 504 is connected to and partially wound about a spool 535 of a first gear and spool assembly 531. The first gear and spool assembly 531 includes both the spool 535 and a first gear 532. The first gear 532 is connected to the spool 535 and therefore they rotate together. Withdrawal of the closure device 500 from the tissue puncture 128 causes the suture 504 to unwind from the spool 535. The spool 535 rotates as the suture 504 unwinds and provides a torsional motive force that is transduced to a linear compacting force.

The torsional motive force provided by the spool 535 is transduced into the linear compacting force by the gearbox assembly 529. The gearbox assembly 529 includes the first gear 532 arranged coaxially with the spool 535. The first gear 532 may be arranged adjacent to a second gear 542. The second gear 542, when assembled, engages the first gear 532. The second gear 542 is arranged on an axis 540. The second gear 542 may be a two-stage gear, with each stage engaging a different adjacent gear as shown. The first and second gears 532 and 542 may engage one another with a frictional fit, or with meshed gear teeth as shown. The second gear 542 is arranged adjacent to a third gear 543 on an axis, 545. When assembled, the second gear 542 engages and drives the third gear 543.

The compaction member 512 preferably includes the teeth shown, which mesh with teeth of the third gear 543. When the spool 535 rotates, it drives the compaction member 512, which in turn compacts the sealing pad 510.

The compaction member 512 is preferably semi-tubular along at least a portion of its length and partially disposed about the suture 504 along its longitudinal axis. The suture 504 and the compaction member 512 are not fixedly connected to one another, allowing each to slide freely past the other. Accordingly, with the anchor 508 deployed, as the closure device 500 is retracted in a first direction with the gearbox assembly 529 in a distal rest position in the housing 552, the suture 504 unwinds from the spool 535, which drives the gearbox assembly 529. The gearbox assembly 529 drives the compaction member 512 in a second, opposite direction, and the compaction member compacts the sealing pad 510.

It will be understood by those of skill in the art having the benefit of this disclosure that the gearbox assembly 529 configuration shown in the figures is exemplary in nature, and not limiting. Any gear configuration (including a single gear) may be used to transmit a motive force generated by retraction of the suture 504 from the closure device 500 to provide an automatic driving force to the sealing pad 510 via the compaction member 512.

The gearbox assembly 529 may be selectably disengageable. Therefore, one or more of the spool 535, first gear 532, second gear 542, and third gear 543 may be movable to disengage or manually disable adjacent gears. For example, one or more of the first gear 532, second gear 542, or third gear 543 may be movable along its respective axis to disengage from an adjacent gear. A biasing member such as a spring 549 is disposed at the second axis 540 biasing the second gear 545 into a meshed relationship with the first and third gears 532, 543. However, the second gear 542 is movable along the second axis 540 by operation of an actuator 551 coupled to the second gear 542. A force may be applied to the actuator 551 (following sliding movement of the gearbox assembly 529, thereby aligning the actuator 551 with an access hole 553 in the handle 552) laterally with respect to the second gear 542, to overcome a biasing force provided by the spring 549 and move or displace the second gear 542 axially out of the meshed or contacting relationship with at least one of the first and third gears 532, 543. According to the embodiment of FIG. 5, axial movement of the second gear 542 only disengages the second gear 542 from the first gear 532. Disengaging the gearbox assembly 529 allows retraction of the closure device 500 and unwinding of the suture 504 from the spool 535 without driving the compaction member 512. The advantages of this disengagement are discussed below with reference to the operation of the closure device 500. The compaction member 512 may interlock with the second gear 542 in a first rack position shown, preventing premature activation of the actuator 551.

When the sealing pad 510 has been sufficiently compacted, the operator can activate a suture cutting assembly to cut the suture 504 within the incision 119. Alternatively, the operator may activate the activator 551 to disengage the gearbox assembly 529 and unwind the suture 504 from the spool 535 as discussed above. The suture cutting assembly may include an actuator 576 exposed for activation by the operator. The suture cutting assembly may be activated in accordance with any of the examples described above with reference to FIGS. 6-12 to cut the suture 504. Unwinding the spool 535 exposes a sufficient length of the suture 504 to allow an operator to easily cut the suture outside the patient to separate the sealing pad 510 and anchor 508 from the remainder of the closure device 500.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
   an anchor, the anchor being rigid and comprising at least one planar surface;
   a sealing pad;
   a compaction member configured to compact the sealing pad toward the anchor;
   a suture coupled to the sealing pad and knotted or tied to the anchor in a pulley-like arrangement, a portion of the suture extending through at least a portion of the compaction member;
   a suture cutting member operable within the compaction member to cut the suture at a location adjacent a distal end portion of the compaction member.

2. The device of claim 1, wherein the compaction member defines a suture path, the suture path exiting the compaction member at an exit aperture along a sidewall of the compaction member.

3. The device of claim 1, wherein the suture cutting member cuts the suture at a location adjacent a distal end portion of the compaction member within a percutaneous incision of a patient.

4. The device of claim 1, wherein the suture cutting member has a generally tubular shape.

5. The device of claim 1, wherein the cutting member is operable to cut the suture within the compaction member.

6. The device of claim 2, wherein the suture path includes at least one change of direction between the distal end of the compaction member and the exit aperture.

7. The device of claim 1, wherein the cutting member is arranged coaxial with the compaction member.

8. The device of claim 1, wherein the cutting member defines a cutting surface at a distal end thereof, the cutting member being operable to cut the suture when advancing distally.

9. A tissue puncture closure device adapted for partial insertion into and sealing of a tissue puncture in an internal tissue wall accessible through a percutaneous incision, the device comprising:
   an anchor disposed on a distal side of the internal tissue wall, the anchor being rigid and comprising at least one planar surface;
   a sealing pad disposed on a proximal side of the internal tissue wall;
   a suture knotted or tied to the anchor in a pulley-like arrangement, the sealing pad being slidably disposed on the suture proximal of the anchor;
   a compaction member positioned proximal of the sealing pad, the compaction member being configured to compact the sealing pad toward the anchor to seal the tissue puncture;
   a suture cutting member arranged parallel with the compaction member and adapted to cut the suture at a location within the percutaneous incision.

10. The tissue puncture closure device of claim 9, further comprising an actuator coupled to the suture cutting member to move the suture cutting member axially relative to the compaction member.

11. The tissue puncture closure device of claim 9, wherein at least a portion of the suture cutting member is operable within the compaction member.

12. The tissue puncture closure device of claim 9, wherein the compaction member defines a suture path and a cutting member path that intersect each other, the suture being positioned in the suture path and the suture cutting member being movable along the cutting member path.

13. The tissue puncture closure device of claim 12, wherein the suture path begins at a distal end of the compaction member and terminates along a sidewall at an outer surface of the compaction member.

14. A compaction assembly adapted for compacting a sealing member of a tissue puncture closure device, comprising:
   a carrier tube;
   a compaction member positioned within the carrier tube and having a distal end portion configured to contact the sealing member;
   a suture path defined at least partially within the compaction member and including at least three changes in direction within the carrier tube, the suture path adapted for passage of a suture member;
   a cutting member path defined in the compaction member, the cutting member path intersecting the suture path;
   a cutting member movable along the cutting member path and operable to cut a suture positioned in the suture path.

15. The compaction assembly of claim 14, wherein the suture path and the cutting member path intersect at a perpendicular angle.

16. The compaction assembly of claim 14, wherein the cutting member is generally tubular and includes a cutting surface at a distal end thereof.

17. The compaction assembly of claim 14, wherein the suture path leads to an exit from the compaction member, the exit being along a sidewall of the compaction member.

18. A method of sealing a tissue puncture in an internal tissue wall accessible through a percutaneous incision using a tissue puncture closure device, the tissue puncture closure device including a rigid anchor having at least one planar surface, a sealing pad, a suture knotted or tied to the anchor in a pulley-like arrangement and coupled to the sealing pad, and a compaction member, the method comprising:
   inserting the tissue puncture closure device into the percutaneous incision;
   deploying the anchor through the tissue puncture;
   advancing the sealing member along the suture toward the surface of the anchor with the compaction member;
   cutting the suture within the compaction member at a location within the percutaneous incision.

19. The method of claim 18, wherein the tissue puncture closure device includes a suture cutting member, and cutting the suture includes moving the suture cutting member within the compaction member.

20. The method of claim 18, wherein the compaction member defines a suture path and a cutting member path that intersect each other, the method further comprising positioning the suture in the suture path and advancing a suture cutting member along the cutting member path.

21. The method of claim 18, wherein cutting the suture includes advancing a tubular cutting member within the compaction member.

22. The method of claim 18, wherein the tissue puncture closure device includes a tension structure configure to maintain the suture in tension during the step of cutting the suture.

* * * * *